United States Patent [19]
Stapp

[11] 3,952,020
[45] Apr. 20, 1976

[54] LACTONE PRODUCTION
[75] Inventor: Paul R. Stapp, Bartlesville, Okla.
[73] Assignee: Phillips Petroleum Company, Bartlesville, Okla.
[22] Filed: Nov. 26, 1973
[21] Appl. No.: 418,914

[52] U.S. Cl............................ 260/343.6; 260/638 R
[51] Int. Cl.²........................................ C07D 307/32
[58] Field of Search.............. 260/343.6, 532, 638 R

[56] References Cited
UNITED STATES PATENTS

| | | | |
|---|---|---|---|
| 3,509,209 | 4/1970 | Fenton............................ | 260/343.6 |
| 3,574,773 | 4/1971 | Mueller et al.................... | 260/638 R |
| 3,769,329 | 10/1973 | Paulik et al...................... | 260/532 |
| 3,816,488 | 6/1974 | Craddock et al................. | 260/532 |
| 3,845,121 | 10/1974 | Eubanks et al................... | 260/532 |

OTHER PUBLICATIONS

Campos et al., Arch. Pharm., 298 (2), 92–100, (1965).
Falbe, Carbon Monoxide in Organic Synthesis, p. 115, (1970).
Houben–Weyl, Methoden Der Organeschen Chemie, Band VI/2, Sauerstoff–Verkendungen I, part 2, p. 608, (1963).

Primary Examiner—Lorraine A. Weinberger
Assistant Examiner—Jane S. Myers

[57] ABSTRACT

Gamma-butyrolactones are prepared by the reaction of carbon monoxide with a 3-alkene-1-ol in the presence of a platinum group metal compound.

3 Claims, No Drawings

LACTONE PRODUCTION

This invention relates to a method for preparing substituted butyrolactones. The substitited butyrolactones are useful in various fields. They are useful in perfumery and can be used as masking odors in many kinds of compositions. They are particularly valuable as chemical intermediates, reacting with alcohols to form esters, with ammonia to form amides, and with other bases, halogen acids and so forth. The esters thus formed are useful as softeners and plasticizers for polymeric materials.

It is therefore an object of this invention to provide a novel process for the preparation of gamma-butyrolactones. Other aspects and objects will be apparent to those skilled in the art from a reading of the specification and appended claims.

In accordance with this invention, it has been discovered that gamma-butyrolactones are prepared by the reaction of a 3-alkene-1-ol with carbon monoxide in the presence of a platinum group metal compound as catalyst.

The process of the present invention can be represented by the following general equation:

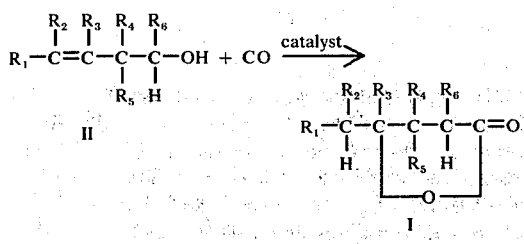

wherein $R_1$, $R_2$, $R_4$ and $R_5$ are hydrogen or an alkyl radical group having from 1 to 3 carbon atoms, $R_3$ is an alkyl radical having from 1 to 3 carbon atoms and $R_6$ is hydrogen or a methyl radical. Examples of the 3alkene-1-ols of formula II which are useful in the practice of this invention include:

3methyl-3-butene-1-ol
2,2,3-trimethyl-3-butene-1-ol
3-methyl-3-heptene-1-ol
3-methyl-4-propyl-3-heptene-1-ol
1-methyl-2,2,3,4-tetrapropyl-3-heptene-1-ol In carrying out the process of this invention, the 3-alkene-1-ol (II) can be formed in situ by the reaction of a suitable olefin and aldehyde. In such instance the reaction proceeds according to the following equation:

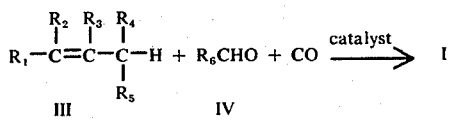

Examples of the olefins of formula III which are useful in the practice of this invention include:

isobutylene
2,4-dimethyl-2-pentene
2-methyl-2-hexene
2,3-dimethyl-2-hexene
2,4,5-tripropyl-4-nonene
and mixtures thereof and the like.

The aldehyde IV can be formaldehyde or acetaldehyde. It is used with olefin III in molar ratios of aldehyde to olefin ranging from 1:1 to 1:10, preferably 1:2 to 1:5.

Carbon monoxide is employed in this invention at partial pressures ranging from 200 to 2000 psig depending upon the type of reactor used, reactivity of the starting materials and the like. The pressure must be sufficient to provide at least stoichiometric amounts of carbon monoxide for the reaction, and where desired, sufficient to maintain the reactants in the liquid phase.

In carrying out the process of this invention, the carboxylic acid corresponding to the lactone can also be prepared.

In the above reaction schemes, when $R_3$ of alcohol (II) or olefin (III) is a methyl or higher radical, the product of the process is predominantly the lactone (I). When $R_3$ is hydrogen, the product of the process is predominantly the corresponding gamma, delta-unsaturated carboxylic acid.

The catalyst system of this invention contains a platinum group metal compound selected from the halides, nitrates, sulfates, oxides and the like of platinum, palladium, ruthenium, rhodium, osmium and iridium. Such metal compounds are employed in amounts ranging from 0.01 to about 10 weight percent of the starting reactants. In a presently preferred embodiment, rhodium chloride is used in amounts ranging from 0.1 to 2 weight percent.

The catalyst system can additionally contain a catalyst activator such as elemental iodine or a lower alkyl iodide. Such activators are employed in amounts ranging from 2 to 6 parts by weight per part of platinum group metal compound.

The process of this invention is carried out in the presence or absence of inert diluent. Aprotic diluents, such as saturated aliphatic, saturated cycloaliphatic or aromatic hydrocarbons, or halogenated hydrocarbons, ethers, esters, nitriles and the like are within the scope of this invention. Such diluents are used in amounts ranging from 1 to 100 parts by weight per part by weight of total reactants.

The process is conducted, continuously or batchhwise, in a pressure vessel, such as an autoclave, wherein reaction pressures can be autogenous. That is, reaction pressure can be self-generated, depending upon the size of the reaction vessel and the quantity and nature of the reactants. Pressure within the reaction zone can range from 200 to 5000 psig, preferably from 200 to 2000 psig. If desired, the pressure can be increased by an inert gas. Reaction time can vary within wide limits and is dependent upon reaction temperature and pressure and on the reactants employed. Reaction times range from 10 minutes to 24 hours.

Reaction temperature is selected according to the reactivity of the reactants and is generally within the range of 25° to 300°C. The products of the process of this invention can be separated and isolated by conventional means of physical or chemical separation known in the art. Selection of such means is within the cognizant skill of one skilled in the art. The following examples illustrate the invention:

EXAMPLE I

To a 1-liter reactor were charged 129 grams of 3-methyl-3-butene-1-ol, 2.0 grams of rhodium chloride trihydrate and 10.3 grams of methyl iodide. The reactor was pressurized to 400 psig with carbon monoxide, then heated to 175°C for 6.5 hours.

After cooling, the reactor was vented and opened. The reaction mixture was washed out of the reaction vessel with benzene and filtered, then distilled. Gamma-isocaprolactone was identified by gas-liquid chromatography (GLC) by comparison to a known sample. The yield of gamma-isocaprolactone was 11%, based on the starting alkenol. This example illustrates that substituted butyrolactones are prepared in accordance with this invention.

EXAMPLE II

To a 1-liter reactor were charged 43 grams of 3-methyl-3-butene-1-ol, 0.5 grams of rhodium chloride trihydrate, 1.1 grams of methyl iodide and 176 grams of benzene. The reactor was pressurized to 1000 psig with carbon monoxide, then heated to 125°C for 6 hours.

After cooling, the reactor was vented and opened. The reaction mixture was filtered, then distilled. The fraction boiling in the range of 106°–109°C at 18 torr was identified as gamma-isocaprolactone by GLC by comparison to a known sample. The yield of gamma-isocaprolactone was 60%, based on starting alkenol.

This example illustrates the increased yield afforded by the use of a diluent in the process of this invention.

EXAMPLE III

To a 1liter reactor were charged 140 grams of isobutylene, 22 grams of 94.4% paraformaldehyde, 0.5 grams of rhodium chloride trihydrate, 2.3 grams of methyl iodide and 176 grams of benzene. The reactor was pressurized to 750 psig with carbon monoxide, then heated to 200°C for 1 hour.

After cooling, the reaction mixture was processed according to the procedure of Example II. The yield of gamma-isocaprolactone was 15%, based on starting paraformaldehyde.

This example illustrates the preparation of a substituted gamma-butyrolactone by the in situ preparation of a 3-alkene-1-ol from an olefin and an aldehyde.

Other modifications or embodiments of this invention will be apparent to those skilled in the art in view of this disclosure. Such modifications or embodiments are within the scope and spirit of the disclosure.

I claim:

1. A process for the preparation of a gamma-butyrolactone having the formula

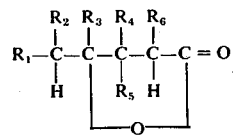

wherein $R_1$, $R_2$, $R_4$ and $R_5$ are individually selected from the group consisting of hydrogen and alkyl of from 1 to 3 carbon atoms, $R_3$ is an alkyl radical having from 1 to 3 carbon atoms and $R_6$ is hydrogen or a methyl radical, which comprises reacting a monoolefin having the formula

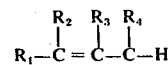

wherein $R_1$-$R_5$ are as defined above, an aldehyde having the formula

wherein $R_6$ is as defined above, and carbon monoxide in the presence of from 0.01 to about 10 weight percent of rhodium chloride based on the weight of starting reactants and from 2 to 6 parts of a catalyst activator selected from the group consisting of elemental iodine and lower alkyl iodides per part by weight of said rhodium chloride.

2. The process of claim 1 wherein there is additionally present an inert aprotic diluent.

3. The process of claim 2 wherein said catalyst is rhodium chloride, said activator is methyl iodide, said olefin is isobutylene, said aldehyde is paraformaldehyde and said diluent is benzene.

* * * * *